(12) United States Patent
Cruz et al.

(10) Patent No.: US 6,797,727 B2
(45) Date of Patent: Sep. 28, 2004

(54) USE OF RHEIN OR DIACERHEIN COMPOUNDS FOR THE TREATMENT OR PREVENTION OF VASCULAR DISEASES

(75) Inventors: Tony Cruz, Toronto (CA); Aleksandra Pastrak, Toronto (CA)

(73) Assignee: Transition Therapeutics Inc., Toronto (CA)

( * ) Notice: Subject to any disclaimer, the term of this patent is extended or adjusted under 35 U.S.C. 154(b) by 86 days.

(21) Appl. No.: 10/196,742

(22) Filed: Jul. 15, 2002

(65) Prior Publication Data

US 2003/0027863 A1 Feb. 6, 2003

Related U.S. Application Data

(60) Provisional application No. 60/306,111, filed on Jul. 16, 2001.

(51) Int. Cl.[7] .................. A61K 31/21; A61K 31/225
(52) U.S. Cl. ..................... 514/510; 514/548
(58) Field of Search .................. 514/510, 548

(56) References Cited

U.S. PATENT DOCUMENTS

| | | |
|---|---|---|
| 4,244,968 A | 1/1981 | Friedman |
| 4,346,103 A | 8/1982 | Friedman |
| 4,950,687 A | 8/1990 | Dall'Asta et al. |
| 5,652,265 A | 7/1997 | Vittori et al. |
| 5,986,129 A | 11/1999 | Di Napoli |
| 6,124,358 A | 9/2000 | Estanove et al. |

FOREIGN PATENT DOCUMENTS

| | | |
|---|---|---|
| EP | 0 809995 | 9/2002 |
| WO | WO 01/85201 A2 | 11/2001 |
| WO | WO 02/05868 A2 | 8/2002 |

OTHER PUBLICATIONS

Carney, SL, "Effects of Diacetyl Rhein on the Development of Experimental Osteoarthritis. A Biochemical Investigation", *Osteoarthritis Cartilage*, 4(4), pp. 251–261 (Dec. 1996).
Felisaz, N., et al., "Stimulating Effect of Diacerein on TGF–beta1 and beta2 Expressing in Articular Chondrocytes Cultured with and without Interleukin", *Osteoarthritis Cartilage*, 7(3), pp. 255–264 (05/99).
French, MH., et al., "Update on Radiation for Restenosis", *Reviews of Cardiovascular Medicine*, 3(1), pp. 1–6 (2002).
Garas, SM, "Overview of Therapies for Prevention of Restenosis After Coronary Interventions", *Pharmacology and Therapeutics*, 93, ppp. 165–178 (2001).

Liistro, F., et al., "First Clinical experience with a Paclitaxel Derivate–Eluting Polymer Stent System Implantation for In–stent Restinosis", *Circulation*, 105(16), pp. 1883–1886 (2002).
Moldovan F., et al., "Diacerhein and Rhein Reduce the ICE–induced IL–1beta and IL–1 Activation in Human Osteoarthritic Cartilage", *Osteoarthritis Cartilage*, 8(3), pp. 186–196 (2000).
Moore, AR, et al., "Effects of Diacerhein on Granuloma Induced Cartilage Breakdown in the Mouse", *Osteoarthritis Cartilage*, 6(1), pp. 19–23, no date available.
Pelletier JP, et al., "Efficacy and Safety of Diacerein in Osteoarthritis of the Knee: a Double–Blind. Placebo Controlled Trial. The Diacerein Study Group", *Arthritis Rhewn*, 43(10), pp. 2339–2348 (Oct. 2000).
Pietragelo, A., "Diacerhein Blocks Iron Regulatory Protein Activation in Inflamed Human Monocytes", *Life Sciences*, 63(14), pp. 213–219 (1998).
Pujol, JP, et al., "Effects of Diacercin on Biocynthesis Activities of Chondrocytes in Culture", *Biorheology*, 37(1–2), pp. 177–184 (2000).
Raines, EW., "The Extracellular Matrix Can Regulate Vascular Cell Migration, Proliferation and Survival", *Int'J of Experimental Pathology*. 81. pp. 173–182 (2000).
Schwartz., SM, "Smooth Muscle Migration in Atherosclerosis and Restinosis", *J of Clinical Investigation*, 99(12), pp. 2814–2817 (1997).
Smith, GN, "Diacerhein Treatment Reduces the Severity of Osteoarthritis in the Canine Cruciate–Deficiency Model of Osteoarthritis", *Arthritis Rheum*, 42(3), pp. 545–554.
Spencer, CM, "Diacerein", *Drugs*, 53(1), pp. 93–106, discussiono n p. 07–108, no date available.
Tamura, T., "Effects of Diacerein on Spontaneous Polyarthritis in Male New Zealand Black/KN Mice", *Osteoarthritis Cartilage*, 7(6), pp. 533–538.
Williams, DO, "Intercoronary Brachytherapy: Past, Present and Future", *Circulation*, 105, pp. 2699–2700, no date available.
Liu, Yanzhu et al., "Inhibiting effect of emodin and rhein on smooth muscle cells proliferation", XP002219154, abstract, 1998.
Kosco–Vilbois M H, "IL–18–a destabilizer of atherosclerotic disease", Trends in Immunology, Elsevier, Cambridge, GB, vol. 23, No. 3, Mar. 1, 2002, p. 123, XP004338937.

*Primary Examiner*—Raymond J. Henley, III
(74) *Attorney, Agent, or Firm*—Fish & Richardson P.C.

(57) ABSTRACT

The present invention relates to the use of rhein or diacerhein compounds to treat and prevent vascular diseases that cause obstruction of the vascular system such as blood vessel restenosis and atherosclerosis.

13 Claims, 2 Drawing Sheets

Figure 1: Effect of diacerhein treatment on smooth muscle cell migration *in vitro*
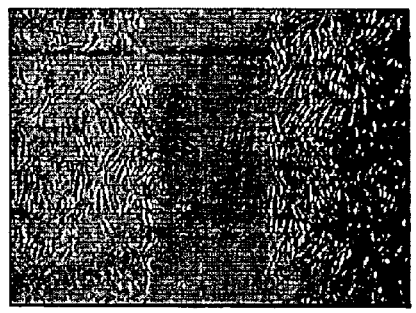
Figure 1-A
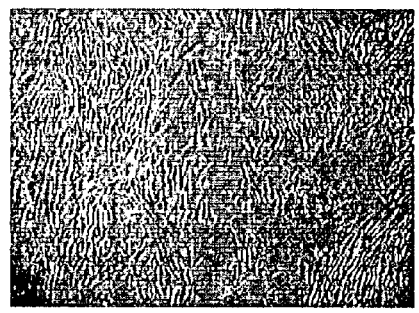
Figure 1- B
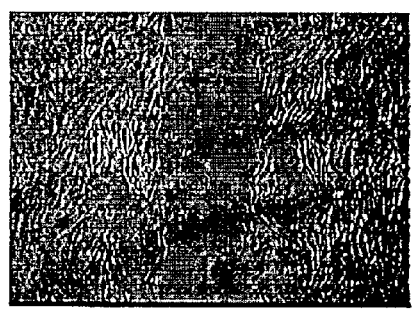
Figure 1-C
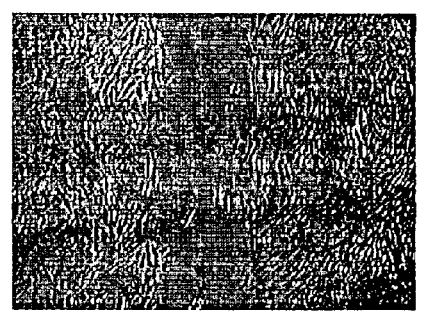
Figure 1-D Figure 2: Effect of prolonged diacerhein or rhein treatment on smooth muscle cell proliferation *in vitro*
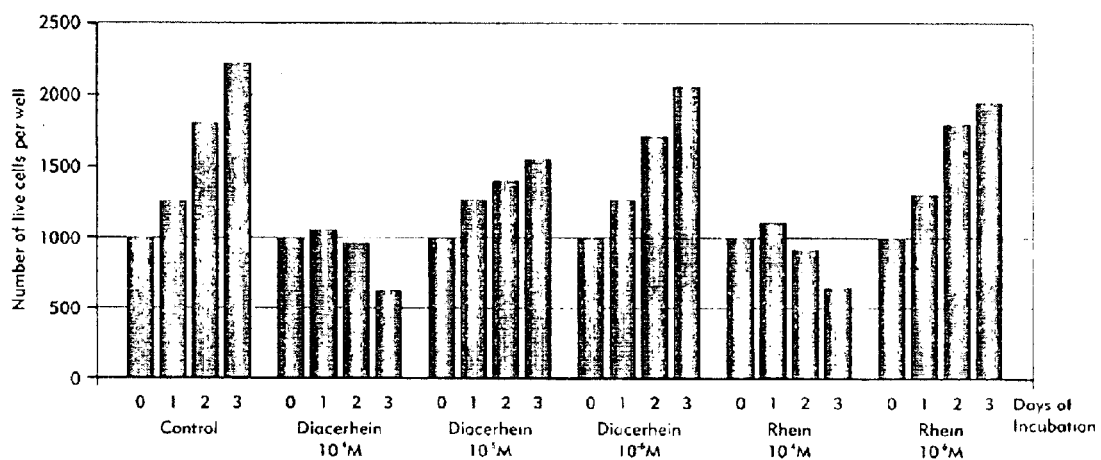

USE OF RHEIN OR DIACERHEIN COMPOUNDS FOR THE TREATMENT OR PREVENTION OF VASCULAR DISEASES

CROSS-REFERENCE TO RELATED APPLICATION

This application claims benefit of U.S. Provisional Patent Application Ser. No. 60/306,111 (filed Jul. 16, 2001). The disclosure of the above application is incorporated herein by reference in its entirety.

FIELD OF THE INVENTION

This invention relates to a method for preventing or treating vascular diseases that cause obstruction of the vascular system such as blood vessel restenosis and atherosclerosis.

BACKGROUND OF THE INVENTION

Rhein and Diacerhein Compounds

Rhein or diacerhein compounds have been described in a large number of publications and patents (Carney, 1996; Pelletier et al., 2000; Spencer et al., 1997; Smith et al., 1999; U.S. Pat. No. 4,950,687; U.S. Pat. No. 4,244,968; U.S. Pat. No. 5,986,129; U.S. Pat. No. 5,652,265; U.S. Pat. No. 6,124,358; European Patent No. 0809995; U.S. Pat. No. 4,346,103; U.S. Pat. No. 4,950,687). Although rhein is the bioactive compound, diacerhein, the acetylated derivative of rhein, enhances bioavailability and has been deemed the drug of choice.

Anti-Arthritic Activity

Rhein or diacerhein compounds are known for their anti-arthritic activity, and have been used clinically for the treatment of osteoarthritis, a degenerative disease resulting in articular cartilage loss with aging. The dosage of treatment is approximately 25 to 200 mg daily, either administered as a single dose or divided into 2 to 4 courses daily. Patients treated have shown marked improvements in the clinical signs of osteoarthritis. There are no significant toxicities associated with rhein or diacerhein compounds, with the exception of a laxative effect found in a significant proportion of patients treated. Most research associated with rhein or diacerhein compounds has focused on attempting to alter administration or formulation to increase absorption and bioavailability, in an attempt to reduce this side effect.

Several studies have investigated the effects of diacerhein on animal models for osteoarthritis, and have consistently demonstrated cartilage protection. These studies used diacerhein dosages ranging around 5 to 50 mg/kg for periods as long as 50 weeks and found that the treatment reduced the severity of osteoarthritis (Carney, 1996; Tamura et al., 1999; Moore et al., 1998).

A large number of in vitro studies using synoviocyte cultures, cartilage explant cultures or chondrocyte cultures or other similar systems have shown that diacerhein may alter the action of interleukin-1 activating enzymes such as ICE, nitric oxide synthesis, TGF-beta synthesis and matrix synthesis (Moldovan et al., 2000; Felisaz et al., 1999; Pujol et al., 2000). Diacerhein stimulates prostaglandin E2 synthesis, an effect not seen in non-steroidal inflammatory agents that are commonly used for the treatment of osteoarthritis and inflammatory diseases. Inhibition of prostaglandin E2 is thought to be necessary for the inhibition of inflammation. Accordingly, diacerhein has been primarily used to treat degenerative diseases such as osteoarthritis rather than inflammatory diseases such as rheumatoid arthritis, wherein diacerhein would be thought to provide the opposite of the intended effect.

Vascular Diseases That Cause Obstruction of the Vascular System

Diacerhein inhibits iron regulatory protein activation in inflamed human monocytes, alters lymphocyte membrane fluidity and alters macrophage activity and neutrophil phagocytosis (Pietrangelo et al., 1998). However, there is no compelling evidence that rhein or diacerhein compounds play a role in treatment of diseases other than osteoarthritis. Specifically absent is any information indicating that rhein or diacerhein compounds play a role in vascular diseases that cause obstruction of the vascular system.

Blood vessel stenosis is a vascular disease that causes obstruction of the vascular system; it may be caused by intimal hyperplasia resulting in atherosclerosis; it may also occur following vascular or coronary interventions.

Blood Vessel Restenosis

Vascular and coronary surgical interventions have become fairly commonplace as methods of treatment of heart disease or diseases of the vasculature. Such interventions include coronary artery bypass surgery, saphenous-vein bypass grafting, perivascular grafting, carotid endarterectomy, reconstructive surgery of arteries that supply lower extremities, heart transplantations, balloon angioplasty, local balloon delivery, endovascular stenting, intravascular stenting, atherectomy or laser ablation carotid endarterectomy, and hemodialysis grafts.

Of these interventions, balloon angioplasty and coronary stents have become some of the most widely used treatments for heart diseases and diseases of the vasculature (such as coronary artery disease). According to the American College of Cardiology, more than 700,000 coronary stent procedures are performed annually in the U.S. When treating coronary artery disease with balloon angioplasty or coronary stents, an ongoing problem has been the high incience of blood vessel restenosis, a recurrence of coronary artery blockage at the site of treatment. Although balloon angioplasty is an effective treatment to open narrowed or blocked coronary arteries, restenosis occur in about 20–50% of cases within 6 months (Garas et al., 2001). Coronary stents, originally seen as a partial solution to the restenosis that occurs with balloon angioplasty, suffer from the same problem, with the major remaining limitation of coronary stenting being that said stents can also become narrowed through restenosis in the first 6 months post-treatment by ingrown tissue growing through the coronary stents.

It has been postulated for several years that applying small amounts of radiation to the area of coronary artery being treated might prevent restenosis. Recently, the first coronary artery radiation system (the Beta-Cath system of Novostre Corp.) has been approved and the use of the system is limited to restenosis occurring in coronary stents. However, there are problems associated with this type of therapy that may lead to more complications over time. For instance, patients who receive intra-coronary radiation appear to have an increased incidence of late coronary artery stenosis. In addition, there have also been observations of appearance of restenosis of the coronary artery at the edges of the radiation field after treatment (French et al., 2002, Williams, 2002). The FDA has urged the long-term monitoring of patients receiving intra-coronary radiation.

To date, the most promising method of preventing restenosis appears to be in the form of drug-eluting coronary stents. A drug-eluting coronary stent is coated with a drug using a coating technology designed to control the release of said drug into the surrounding tissue. The intention of this time-release process is to slow down the growth of unwanted cells (restenosis) and allow the vessel to heal.

Currently, there are several drug-coated stents either in early clinical trials or that have been recently approved; these include rapamycin, paclitaxel and actinomycin-D coated stents. However, recent clinical findings have revealed disappointing results for some of the drug-eluting stent studies. In the paclitaxel derivative-eluting stent study, restenosis rate increased to greater than 60% after a 12-month follow up (Liistro et al., 2002). Guidant has also recently halted further clinical development of actinomycin-D eluting stents because clinical trials revealed the ineffectiveness of actinomycin D in preventing restenosis. Patients treated with actinomycin-D eluting stents have an unacceptably high target lesion revascularization rate (Guidant website, Mar. 7, 2002).

Atherosclerosis

Cardiovascular disease is a serious problem and accounts for 44% of the mortality in the USA. Atherosclerotic cardiovascular disease is a generalized process that involves the brain, heart, and peripheral arteries. Atherosclerosis is characterized by intimal thickening caused by the accumulation of cells, infiltration of inflammatory cells, lipids and connective tissues that can lead to cardiac and cerebral infarction (such as heart attack and stroke). Atherosclerosis is characterized by occlusion of an artery, leading to a series of clinical complications such as myocardial infarction and stroke. Prevention of the occlusion of the artery, by preventing the migration of cells to said artery or by preventing the proliferation of cells within the cell wall of said artery, will result in the prevention or treatment of this disease thereby reducing the incidences of clinical complications arising from this disease.

Needs

Accordingly, there is a need for the development of superior treatments for vascular diseases that cause obstruction of the vascular system such as blood vessel restenosis following vascular and coronary intervention and atherosclerosis.

In summary, there is no published information indicating that rhein or diacerhein compounds play a role in the treatment or prevention of vascular diseases that cause obstruction of the vascular system such as blood vessel restenosis and atherosclerosis.

SUMMARY OF THE INVENTION

It is therefore an object of the present invention to provide a therapy using rhein or diacerhein compounds to treat and prevent vascular diseases that cause obstruction of the vascular system such as blood vessel restenosis and atherosclerosis.

One aspect of the present invention is a composition comprising of (1) an agent selected from a group consisting of rhein, diacerhein, analogs of rhein, analogs of diacerhein, homologues of rhein, homologues of diacerhein, derivatives of rhein, derivatives of diacerhein, salts of rhein, salts of diacerhein, esters of rhein, esters of diacerhein, amides of rhein, amides of diacerhein, prodrugs of rhein, and prodrugs of diacerhein, and (2) a pharmaceutically acceptable carrier, for use in the treatment or prevention of a vascular disease that causes obstruction of the vascular system, such as blood vessel restenosis or atherosclerosis.

Another aspect of this invention is said composition wherein said pharmaceutically acceptable carrier is designed for oral or injected administration of said composition, or wherein said composition is incorporated into a polymer or a non-polymeric carrier.

Yet another aspect of this invention is the use of an agent selected from a group consisting of rhein, diacerhein, analogs of rhein, analogs of diacerhein, homologues of rhein, homologues of diacerhein, derivatives of rhein, derivatives of diacerhein, salts of rhein, salts of diacerhein, esters of rhein, esters of diacerhein, amides of rhein, amides of diacerhein, prodrugs of rhein and prodrugs of diacerhein for the treatment or prevention of a vascular disease that causes obstruction of the vascular system such as blood vessel restenosis or atherosclerosis.

Yet another aspect of this invention is said use wherein said agent is administered locally, systemically, orally, nasally, parenterally, topically, transdermally, rectally, or endoluminally.

Yet another aspect of this invention is said use wherein the dose of said agent is between about 0.1 mg/kg/day and about 10 mg/kg/day.

Yet another aspect of this invention is said use wherein a medical device, such as an implant, a stent, a stent graft, a vascular graft, an indwelling catheter, one or more sutures, a catheter, a local delivery balloon, or a prosthesis, is coated, embedded or impregnated with said agent.

Yet another aspect of this invention is said use wherein said agent is incorporated into a polymer or a non-polymeric carrier.

BRIEF DESCRIPTION OF DRAWINGS

FIG. 1-A is a photograph of the control at 0 h in an in vitro assay of smooth muscle cells migration.

FIG. 1-B is photograph of the control at 26 h in an in vitro assay of smooth muscle cells migration.

FIG. 1-C is a photograph of cells treated with ($1 \times 1^{-4}$ M) of diacerhein at 26 h in an in vitro assay of smooth muscle cells migration.

FIG. 1-D is a photograph of cells treated with ($5 \times 10^{-5}$ M) of diacerhein at 26 h in an in vitro assay of smooth muscle cells migration.

FIG. 2 is a graph showing the effect on prolonged rhein or diacerhein treatment on the proliferative activity of smooth muscle cells.

DETAILED DESCRIPTION OF THE INVENTION

Definitions

Prior to setting forth the invention, it may be helpful to an understanding thereof to first set forth definitions of certain terms that will be used hereinafter.

"Atherosclerosis" is a cardiovascular disease that involves the brain, heart and peripheral arteries. Atherosclerosis is characterized by intimal thickening caused by the accumulation of cells, infiltration of inflammatory cells, lipids and connective tissues that can lead to cardiac and cerebral infarction (such as heart attack and stroke).

"Blood vessel restenosis" means a recurrence of artery blockage at a site of therapeutic intervention of vascular disease. Vascular diseases (such as atherosclerosis) are a leading cause of death and disability in the developed world. Several therapeutic interventions have been developed to treat vascular diseases; these therapeutic interventions include atherectomy, balloon angioplasty, insertion of stents, and insertion of arterial and venous grafts. Restenosis is characterized by thickening of the blood vessel wall in response to injury or trauma caused by these therapeutic interventions.

"Diacerhein" is a diacetylated derivative of rhein. Diacerhein possesses the following chemical and non-chemical names: 4,5-bis(acetyloxy)-9,10-dihydro-4,5dihydroxy-9,10- dioxo-2-anthracenecarboxylic acid, 4,5-diacetoxy-9,10-dioxo-9,10-dihydroanthracene-2-carboxylic acid, 4,5-Bis(acetyloxy)-9,10-dihydro-9,10-dioxo-2-anthracenecarboxylic acid, 9,10-dihydro-4,5-dihydroxy-9,10-dioxo-2-anthroic acid diacetate, 1,8-diacetoxy-3-carboxyanthraquinone, diacerein and diacetyl rhein.

"Osteoarthritis" is a slowly progressive degeneration of the articular cartilage that manifests in the weight-bearing joints such as the knees and hips. Osteoarthritis is characterized by narrowing of the joint owing to the loss of articular cartilage and thickening of the subchondral bone. The term "osteoarthritis" when used in this specification includes osteoarthritis-related conditions.

"Rhein" is the common name that describes the anthraquinone present in rhubarb (Rhei rhizoma). Rhein possesses the following chemical and non-chemical names: 9,10-dihydro-4,5-dihydroxy-9,10-dioxo-2-anthracenecarboxylic acid; 1,8-dihydroxyanthraquinone-3-carboxylic acid; 4,5-dihydroxyanthraquinone-2-carboxylic acid; chrysazin-3-carboxylic acid; monorhein; rheic acid; cassic acid; arietic acid; and rhubarb yellow.

"Rhein or diacerhein compounds" means rhein and diacerhein, as well as analogs, homologues, derivatives, salts, esters, amides and prodrugs of rhein or diacerhein. Several patents describe analogs and derivatives of rhein or diacerhein that enhance efficacy, increase solubility and bioavailability for human use (U.S. Pat. No 4,244,968; U.S. Pat. No. 5,986,129; U.S. Pat. No. 5,652,265). The increased solubility and bioavailability has been improved by means of surfactants, water-soluble polymers and micronization techniques (U.S. Pat. No. 6,124,358; European Patent 0809995). Numerous other rhein related derivatives are described in a patent for the use of anthraquinone derivatives for use in arthritis (U.S. Pat. No. 4,346,103). Further, water-soluble formulations for intra-articular injections have also been described (U.S. Pat. No. 4,950,687). It would be known to anyone skilled in the art that other minor modifications to the structure of rhein or diacerhein would be considered to be derivatives of rhein and diacerhein, and would likely to have similar biochemical effects as those disclosed in this invention. Similarly, since the tertiary structures of rhein and diacerhein are well known, it would be known to anyone skilled in the art that a structure with a similar tertiary shape as rhein or diacerhein (though chemically quite different) would be known as an analog of rhein or diacerhein and would be predicted to have similar biochemical effects as those disclosed in this invention. A prodrug is a compound that gets converted to rhein, diacerhein, or an analog, homologue, derivative, salt, ester, or amide of rhein or diacerhein either through a naturally occuring biochemical event within the patient, or through the use of a secondary compound that triggers or facilitates the change.

"Vascular disease that causes obstruction of the vascular system" means any vascular disease that has the effect of obstructing a blood vessel. This descriptive term includes within its scope blood vessel stenosis, blood vessel restenosis, atherosclerosis, as well as obstruction caused by intimal hyperplasia.

The present invention comprises administration of a pharmaceutical composition containing a diacerhein or rhein compound to a patient for treatment or prevention of vascular diseases that cause obstruction of the vascular system such as blood vessel restenosis and atherosclerosis.

An active ingredient in the pharmaceutical composition may contain one or more diacerhein or rhein compound.

Any pharmaceutically acceptable formulation containing at least one rhein or diacerhein compound may be used, including tablets, solutions, powders, suspensions, suppositories, creams, or aerosols. Any pharmaceutically acceptable carriers known or anticipated in the art may be added to the formulation. For instance, diacerhein-containing formulations could possibly include the use of hydrogel matrices based on hydrophilic polysaccharides, such as pectins and alginates (EP 0809 995).

The composition may be administered using any means known in the art, such as orally, nasally, parenterally, topically, transdermally, or rectally. Also within the scope of the invention is release of the active ingredient from a surgical or medical device or implant, such as stents, sutures, catheters, prosthesis and the like. The device may be coated, embedded or impregnated with the compound. The compositions of the present invention may be also formed as a film.

Injectable Dosage Form

Rhein or diacerhein compounds may be used for the treatment of vascular diseases that cause obstruction of the vascular system such as blood vessel restenosis and atherosclerosis. A therapeutically effective dose of rhein or diacerhein compound can be administered parenterally.

Parenteral administration, if used, is generally characterized by injection. Injectable formulations can be prepared in conventional forms, either as liquid suspension or solutions, solid forms suitable for solubilization in liquid prior to injection, or as emulsions, by any method or means known or anticipated in the art. Parenteral administration may also involve a slow release or sustained release system. Administration may also be by continuous infusion or bolus dosing sufficient to maintain therapeutic levels. Preferably, administration of rhein or diacerhein compounds would be used at least in the course of the events leading to restenosis if possible and continued thereafter for a time sufficient to permit proper healing of the vasculature, or for approximately two to three weeks. A longer administration time may also be advantageous.

The precise therapeutically effective amount of rhein or diacerhein compound depends on individual differences in age, weight, extent of atheromatous plaque development, the condition of the patient, and on the compound utilized. Generally, rhein or diacerhein compounds should be preferably administered in an amount of at least 0.25 mg/kg per injectable dose, more preferably in an amount up to 5 mg/kg per dose. The effective daily dose may be divided into multiple doses. The total daily dose of the compounds of this invention administered to a human may range from about 0.5 to about 10 mg/kg/day.

Oral Dosage Form

For oral administration, the composition will generally take the form of a tablet or a capsule. The formulation of tablets and capsules containing a known active ingredient is a skill well known and established in the art. Generally, tablets and capsules for oral use will generally include one or more commonly used carriers such as lactose or corn starch. Other optional components for incorporation into an oral formulation may include preservatives, suspending agents, thickening agents, and the like.

For purposes of oral administration preferable doses may be in the range of from about 0.1 to about 10 mg/kg/day. If desired, the effective daily dose may be divided into multiple doses for purposes of administration; consequently, single dose compositions may contain such amounts or submultiples thereof to make up the daily dose. "Extended release" formulations may provide the opposite effect, with administration less frequently than once daily and single dose compositions thereof containing multiples of a daily dose.

Release of Composition from Medical Devices

The active compound may be covalently linked or mixed or encapsulated in microcapsules with either polymeric or non-polymeric formulations which may coat, embed or impregnate or otherwise contact a medical device that is commercially available or is in research and development phase such as an implant, stent, stent graft, vascular graft, indwelling catheter, sutures, catheter, prosthesis and the like.

In other cases, the active compound may contact a medical device such as an implant, stent, stent graft, vascular graft, local balloon delivery, indwelling catheter, sutures, catheter, prosthesis and the like without any formulations. Carriers can be either commercially available or in research and development phase. Representative examples of carriers include poly(ethylene-vinyl acetate), copolymers of lactic acid and glycolic acid, methacrylate co-polymer, poly (caprolactone), poly(lactic acid), copolymers of poly(lactic acid and caprolactone), gelatin, hyaluronic acid, collagen matrices, cellulose, starch, casein, dextran, polysaccharides, fibrinogen, vitamin B12 and albumin, silicone rubber, acrylic polymers, polyethylene, polyproplene, polyamides, polyurethane, vinyl polymers, poly(ethylene-vinyl acetate) copolymers. Polymeric or non-polymeric carriers may be fashioned in a variety of forms to possess desired release characteristics and/or specific desired properties in response to a specific triggering event such as temperature or pH changes.

In the case of a stent, the therapeutically effective amount of principal active compound to be administered to the intimal or lumenal layer of arterial walls may be up to about 50 mg.

EXAMPLES

The examples below are designed to demonstrate but not limit the embodiments of the present invention.

Example 1

Effect of Diacerhein of Smooth Muscle Cell Migration—in vitro Assay of Biological Activity The following in vitro assay was conducted to illustrate the effect of diacerhein on smooth muscle cell migration. Increased smooth muscle cell migration following injury is one of the predominant causes of obstruction of the vascular system following stenting and other vascular procedures.

Rat aortic smooth muscle cells (A-10 cells) were seeded at $2.5 \times 10^5$ cells/well in 6 well plates using Dulbecco's Modified Eagle Medium™ (Gibco BRL Cat. # 11885-084), 10% FBS and 1% Antibiotic Antimycotic (Gibco BRL Cat. # 15240). Confluency of cells after about 8 h was between 80~90%. Cells were injured with the single edge cell scraper (one injury/well) then washed twice with PBS and treated with diacerhein at concentrations ranging from 50 $\mu$M to 100 $\mu$M. Images were taken using a X5 modulation objective (Zeiss, Germany) attached to a Zeiss Axiovert 100 inverted microscope equipped with Hoffman Modulation contrast optical filters (Greenvale, N.Y.).

Results are shown in FIGS. 1(A–D). The images were taken at zero time and following the incubation of smooth muscle cells with diacerhein for a period of 20 h. The migration of smooth muscle cells was significantly inhibited in the presence of diacerhein at concentrations of 50 $\mu$m and 100 $\mu$M; demonstrated in FIGS. 1-C and 1-D, respectively.

The results of the assay demonstrate that diacerhein is an efficient inhibitor of smooth muscle cell migration in vitro and thus can serve as an endogenous inhibitor of smooth muscle cell migration in the intimal lesion after injury. Migration of smooth muscle cells is one of the predominant mechanisms of action in vascular diseases causing obstruction of the vascular system. Specifically, smooth muscle cell migration is a major cause of blood vessel restenosis, as well as a contributor to atherosclerosis. (For a review, see Schwartz, 1997, Raines, 2000). Therefore, rhein or diacerhein is predicted to effectively treat these disease states.

Example 2

Effect of Diacerhein and Rhein on Smooth Muscle Cell Proliferation—In vitro Assay of Biological Activity The following in vitro assay was conducted to illustrate the effect of diacerhein and rhein on smooth muscle cell proliferation. Increased smooth muscle proliferation is well known to be central to the etiology of vascular diseases causing obstruction of the vascular system such as atherosclerosis and restenosis (For a review, see Schwartz, 1997, Raines, 2000).

A-10 cells were seeded at $1.0 \times 10^3$ cells/well in 96 well plates using Dulbecco's Modified Eagle Medium™ (Gibco BRL Cat. # 11885-084), 10% FBS and 1% Antibiotic Antimycotic (Gibco BRL Cat. # 15240) and allowed to grow overnight. Prior to treatment, cells were washed and the culture medium was replaced with culture medium containing either rhein or diacerhein at varying concentrations ranging from $10^{-4}$ to $10^{-8}$M.

The CellTiter 96® AQ$_{ueous}$ One Solution Cell Proliferation Assay (Promega) was used as a colorimetric method for determining the number of viable cells in proliferation. Cell proliferation assays were performed by adding a small amount of the CellTiter 96® AQ$_{ueous}$ One Solution Reagent directly to culture wells, incubating for 1–4 hours and then recording absorbance at 490 nm with a 96 well plate reader. The quantity of formazan product as measured by the amount of 490 nm absorbance is known in the art to be directly proportional to the number of living cells in the culture. For the assay, cells were incubated with rhein or diacerhein for 24 h. In addition, cells from selected concentrations are also treated with rhein or diacerhein and are incubated for 1–3 days. The cells are harvested and counted using a hemocytometer. Trypan blue staining was carried out to determine % of viable cells vs dead cells.

As measured by the CellTiter Proliferation Assay, treatment of either rhein or diacerhein at concentration higher than $10^{-7}$ M resulted in a decrease in proliferative activity as compared to untreated cells (Table 1). In addition, prolonged incubation studies conducted also demonstrated the antiproliferative activity of rhein or diacerhein on aortic smooth muscle cells (FIG. 2). Intimal smooth muscle cell (SMC) proliferation plays a key role in atherosclerosis and restenosis following vascular injury. Therefore, rhein or diacerhein is predicted to effectively treat these disease states.

Summary of Examples

In summary, these examples clearly demonstrate that a rhein or diacerhein compound effectively reduces both smooth muscle cell migration and smooth muscle cell proliferation—two factors that play a key role in atherosclerosis, restenosis, and other vascular diseases that cause obstruction of the vascular system. Thus, these examples clearly demonstrate that a rhein or diacerhein compound can be used to effectively treat or prevent vascular diseases that cause obstruction of the vascular system.

Although the invention has been described with preferred embodiments, it is to be understood that modifications may be resorted to as will be apparent to those skilled in the art. Such modifications and variations are to be considered within the purview and scope of the present invention.

TABLE 1

Effect of rhein or diacerhein treatment on cellular proliferation in a smooth muscle cell line

| Treatment | Measure of Proliferative (Absorbance at 490 nm) | Activity Percentage of viable cells |
|---|---|---|
| No treatment | 0.775 | 96.2% |
| Diacerhein | | |
| Treatment with $10^{-4}$M | 0.380 | 97.0% |
| Treatment with $7.5 \times 10^{-5}$M | 0.408 | N/a |
| Treatment with $5.0 \times 10^{-5}$M | 0.419 | N/a |
| Treatment with $2.5 \times 10^{-5}$M | 0.561 | N/a |
| Treatment with $10^{-5}$M | 0.646 | 97.5% |
| Treatment with $10^{-6}$M | 0.710 | 96.2% |
| Treatment with $10^{-7}$M | 0.738 | N/a |
| Rhein | | |
| Treatment with $10^{-4}$M | 0.430 | 97.1% |
| Treatment with $7.5 \times 10^{-5}$M | 0.460 | N/a |
| Treatment with $5.0 \times 10^{-5}$M | 0.518 | N/a |
| Treatment with $2.5 \times 10^{-5}$M | 0.577 | N/a |
| Treatment with $10^{-5}$M | 0.675 | 96.0% |
| Treatment with $10^{-6}$M | 0.738 | 97.5% |
| Treatment with $10^{-7}$M | 0.891 | N/a |

References

Carney S L. Effects of diacetyl rhein on the development of experimental osteoarthritis: A biochemical investigation. Osteoarthritis Cartilage 1996 4(4): 251–261

Felisaz N, Boumediene K, Ghayor C, Herrouin J F, Bogdanowicz P, Gale P, Pujo J P. Stimulating effect of diacerein on TGF-beta1 and beta2 expressing in articular chondrocytes cultured with and without interleukin. Osteoarthritis Cartilage 1999 7(3): 255–264

French M H, Faxon D P. Update on radiation for restenosis. Reviews in Cardiovascular Medicine 2002 3(1): 1–6

Garas S M, Huber P, Scott N A. Overview of therapies for prevention of restenosis after coronary interventions. Pharmacology and Therapeutics 2001 92:165–178

Liistro F, Stankovic G, Di Mario C, Takagi T, Chieffo A, Moshiri S, Montorfano M, Carlino M, Briguori C, Pagnotta P, Albiero R, Corvaja N, Colombo A. First clinical experience with a paclitaxel derivate-eluting polymer stent system implantation for in-stent restenosis: immediate and long-term clinical and angiographic outcome. Circulation 2002 105(16):1883–6

Moldovan F, Pelletier J P, Jolicoeur F C, Cloutier J M, Martel-Pelletier j. Diacerhein and rhein reduce the ICE-induced IL-1beta and IL-1 activation in human osteoarthritic cartilage. Osteoarthritis Cartilage 2000 8(3): 186–196

Moore A R., Greenslade K J, Alam C A, Willoughby D A. Effects of diacerhein on granuloma induced cartilage breakdown in the mouse. Osteoarthritis Cartilage 6(1): 19–23

Pelletier J P, Yaron M, Haraoui B, Cohen P, Nahir M A, Choquette D, Wigler I, Rosner I A, Beaulieu A D. Efficacy and safety of diacerein in osteoarthritis of the knee: a double-blind, placebo controlled trial. The Diacerein Study Group. Arthritis and Rheumatism 2000 43(10): 2339–2348

Pietrangelo A, Montosi G, Recalcati S, Garuti C, Cairo G. Diacerhein blocks iron regulatory protein activation in inflamed human monocytes. Life Sciences 1998 63(14): 213–219

Pujol J P, Felisaz N, Boumediene K, Ghayor C, Herrouin J F, Bogdanowicz P, Galcra P. Effects of diacerein on biosynthesis activities of chondrocytes in culture. Biorheology 2000 37(1–2): 177–184

Raines, E W. The extracellular matrix can regulate vascular cell migration, proliferation and survival. International Journal of Experimental Pathology 2000 81:173–182

Schwartz, S M. Smooth Muscle Migration in Atherosclerosis and Restenosis. Journal of Clinical Investigation. 1997 99(12): 2814–2817

Smith G. N. Jr, Myers, S, Brandt K D, Mickler E A, Albrecht M E. Diacerhein treatment reduces the severity of osteoarthritis in the canine cruciate-deficiency model of osteoarthritis. Arthritis and Rheumatism 42(3): 545–554

Spencer C. M., Wilde M. I. Diacerein. Drugs 53(1): 93–106, discussion 107–108

Tamura T, Ohmori K, Nakamura K. Effects of diacerein on spontaneous polyarthritis in male New Zealand black/KN mice. Osteoarthritis Cartilage 1999 7(6): 533–538

Williams D O. Intracoronary brachytherapy: Past, Present and Future. Circulation 105:2699–2700

We claim:

1. A medical device which is coated, imbedded, or impregnated with an agent selected from a group consisting of rhein, diacerhein, analogs of rhein, analogs of diacerhein, homologues of rhein, homologues of diacerhein, derivatives of rhein, derivatives of diacerhein, salts of rhein, salts of diacerhein, esters of rhein, esters of diacerhein, amides of rhein, amides of diacerhein, prodrugs of rhein and prodrugs of diacerhein.

2. The medical device of claim 1 wherein said agent is in a polymeric or non-polymeric carrier.

3. The medical device of claim 1 wherein said medical device is selected from the group consisting of an implant, a stent, a stent graft, a vascular graft, an indwelling catheter, sutures, a catheter, local delivery balloon and a prosthesis.

4. The medical device of claim 1 wherein the amount of agent administered is up to about 50 mg and wherein the medical device is a stent.

5. A method of treating a disease or condition selected from the group consisting of a vascular disease that causes obstruction of the vascular system, atherosclerosis and blood vessel restenosis comprising administering to a subject in need thereof an agent selected from a group consisting of rhein, diacerhein, analogs of rhein, analogs of diacerhein, homologues of rhein, homologues of diacerhein, derivatives of rhein, derivatives of diacerhein, salts of rhein, salts of diacerhein, esters of rhein, esters of diacerhein, amides of rhein, amides of diacerhein, prodrugs of rhein and prodrugs of diacerhein.

6. The method of claim 5 wherein said agent is administered locally.

7. The method of claim 5 wherein said agent is administered systemically.

8. The method of claim 5 wherein said agent is administered by a method selected from a group consisting of orally, nasally, parenterally, topically, transdermally, rectally, and endoluminally.

9. The method of claim 5 wherein the dose of said agent is between about 0.1 mg/kg/day to about 10 mg/kg/day.

10. The method of claim 5 wherein administration is via a medical device coated, imbedded, or impregnated with said agent.

11. The method according to claim 10 wherein said medical device is selected from the group consisting of an implant, a stent, a stent graft, a vascular graft, an indwelling catheter, sutures, a catheter, local delivery balloon and a prosthesis.

12. The method according to claim 10 wherein said agent is incorporated into a polymer.

13. The method according to claim 10 wherein said agent is incorporated into a non-polymeric carrier.

* * * * *

UNITED STATES PATENT AND TRADEMARK OFFICE
CERTIFICATE OF CORRECTION

PATENT NO. : 6,797,727 B2  Page 1 of 1
DATED : September 28, 2004
INVENTOR(S) : Antonio Cruz and Aleksandra Pastrak It is certified that error appears in the above-identified patent and that said Letters Patent is hereby corrected as shown below:

<u>Column 10,</u>
Please delete lines 17-33.

Signed and Sealed this

Twenty-second Day of February, 2005

JON W. DUDAS
*Director of the United States Patent and Trademark Office*